United States Patent
Watanabe et al.

(10) Patent No.: US 11,554,133 B2
(45) Date of Patent: Jan. 17, 2023

(54) BILE ACID SYNTHESIS PROMOTER, COMPOSITION FOR PROMOTING BILE ACID SYNTHESIS AND FOOD COMPOSITION FOR PROMOTING BILE ACID SYNTHESIS

(71) Applicant: KRACIE HOLDINGS, LTD., Tokyo (JP)

(72) Inventors: Shimpei Watanabe, Tokyo (JP); Satoshi Inamasu, Tokyo (JP); Mitsuhiro Watanabe, Kanagawa (JP); Yoko Takashina, Kanagawa (JP)

(73) Assignee: KRACIE HOLDINGS, LTD., Tokyo (JP)

( * ) Notice: Subject to any disclaimer, the term of this patent is extended or adjusted under 35 U.S.C. 154(b) by 0 days.

(21) Appl. No.: 17/171,545

(22) Filed: Feb. 9, 2021

(65) Prior Publication Data
US 2021/0161931 A1 Jun. 3, 2021

Related U.S. Application Data

(62) Division of application No. 16/493,906, filed as application No. PCT/JP2018/005630 on Feb. 19, 2018, now abandoned.

(30) Foreign Application Priority Data
Mar. 16, 2017 (JP) .............................. JP2017-050744

(51) Int. Cl.
*A61K 31/7048* (2006.01)
*A61P 1/16* (2006.01)
*A61K 31/365* (2006.01)

(52) U.S. Cl.
CPC ........ *A61K 31/7048* (2013.01); *A61K 31/365* (2013.01); *A61P 1/16* (2018.01)

(58) Field of Classification Search
None
See application file for complete search history.

(56) References Cited

U.S. PATENT DOCUMENTS

2019/0099400 A1* 4/2019 Watanabe ................. A61P 3/04

FOREIGN PATENT DOCUMENTS

| CN | 101002815 A | 7/2007 |
|---|---|---|
| CN | 103479616 A | 1/2014 |
| CN | 105194421 A | 12/2015 |
| CN | 105 982 887 A | 10/2016 |
| JP | 2008-297209 A | 12/2008 |
| JP | 2010-95456 A | 4/2010 |
| KR | 10-2014-0034645 | 3/2016 |
| WO | 2017/061559 A1 | 4/2017 |

OTHER PUBLICATIONS

Yamashita, JP 2008297209A, Dec. 11, 2008, machine translation. (Year: 2008).*
Zhao, CN 103479616A, Jan. 1, 2014, machine translation. (Year: 2014).*
Esumi, WO 2017/061559 A1, filed Sep. 10, 2015, machine translation. (Year: 2017).*
Xu et al., "Arctigenin Promotes Cholesterol Efflux from THP-1 Macrophages Through PPAR-γ/LXR-α Signaling Pathway", *Biochem. Biophys. Res. Commun.*, vol. 441, pp. 321-326 (2013).
Cho et al., "Effects of Forsythia Fruit Extracts and Lignan on Lipid Metabolism ", *BioFactors*, vol. 22, pp. 161-163 (2004).
Han et al., "Anti-obesity Effects of Arctii Fructus (*Arctium lappa*) in White/brown Adipocytes and High-fat Diet-induced Obese Mice", *Food Funct.*, vol. 7, pp. 5025-5033 (2016).
Xiang et al., "Effects of Arctigenin on α-Glucosidase Activity", *Modern Chinese Medicine*, vol. 11, No. 5, pp. 28-29 (2009), along with an English-language translation and Abstract.
Miyazawa et al., "Inhibitory Compounds of α-Glucosidase Activity from *Arctium lappa* L.", *J. Oleo Sci.*, vol. 54, No. 11, pp. 589-594 (2005).
Bartram et al., "Effect of Starch Malabsorption on Fecal Bile Acids and Neutral Sterols in Humans: Possible Implications for Colonic Carcinogenesis ", *Cancer Res.*, vol. 51, pp. 4238-4242 (1991).
Kong et al., "Mechanism of Tissue-specific Farnesoid X Receptor in Suppressing the Expression of Genes in Bile-acid Synthesis in Mice", *Hepatology*, vol. 56, No. 3, pp. 1034-1043 (2012).
International Search Report issued in PCT/JP2018/005630, dated Apr. 10, 2018, along with an English-language translation.
Written Opinion of the International Search Authority issued in PCT/JP2018/005630, dated Apr. 10, 2018, along with an English-language translation.
Fan et al., "Arctigenin Protects Focal Cerebral Ischemia-Reperfusion Rats Through Inhibiting Neuroinflammation", *Biol. Pharm. Bull*, vol. 35, No. 11, pp. 2004-2009 (2012).
Extended European Search Report issued in EP Patent Application No. 18767701.8, dated Oct. 20, 2020.
Communication under 94(3) EPC from EP Patent Office Application No. 18 767 702.8, dated Oct. 14, 2021.
Notice of Reasons for Rejection issued in TW Patent Application No., dated Sep. 23, 2021, English translation.
Yoshibayashi Vegetables "The Indication of Gobo Tea," 2012, vol. 11, English translation.

* cited by examiner

*Primary Examiner* — Layla D Berry
(74) *Attorney, Agent, or Firm* — Greenblum & Bernstein, P.L.C.

(57) ABSTRACT

[Problem] To provide a novel medicine that is capable of promoting cholesterol metabolism to thereby treat, ameliorate or prevent various symptoms associated with increase in blood cholesterol level. [Solution] The present inventors newly found that arctigenin has an effect of promoting the conversion of cholesterol into bile acid. The present invention provides a bile acid synthesis promoter, a composition for promoting bile acid synthesis and a food composition for promoting bile acid synthesis each comprising arctigenin and/or arctiin as active ingredient(s).

4 Claims, 3 Drawing Sheets

Specification includes a Sequence Listing.

SEQUENCE LISTING

```
<160> NUMBER OF SEQ ID NOS: 12

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence : Synthetic
      nucleotide (18S-F)
```

<400> SEQUENCE: 1
ttctggccaa cggtctagac aac                                                23

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence : Synthetic
      nucleotide (18S-R)

<400> SEQUENCE: 2
ccagtggtct tggtgtgctg a                                                  21

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence : Synthetic
      nucleotide (Cyp8b1-F)

<400> SEQUENCE: 3
ggaagccaag aagtcgttca                                                    20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence : Synthetic
      nucleotide (Cyp8b1-R)

<400> SEQUENCE: 4
gacgcagact ctcctccatc                                                    20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence : Synthetic
      nucleotide (SHP-F)

<400> SEQUENCE: 5
caaggagtat gcgtacctga ag                                                 22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence : Synthetic
      nucleotide (SHP-R)

<400> SEQUENCE: 6
ggctccaaga cttcacacag t                                                  21

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence : Synthetic
      nucleotide (FXR-F)

```
<400> SEQUENCE: 7
caaaatgact caggaggagt acg                                              23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence : Synthetic
      nucleotide (FXR-R)

<400> SEQUENCE: 8
gcctctctgt ccttgatgta ttg                                              23

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence : Synthetic
      nucleotide (FGF4R-F)

<400> SEQUENCE: 9
gaggcatgca gtatctgg                                                    18

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence : Synthetic
      nucleotide (FGF4R -R)

<400> SEQUENCE: 10
caaagtcagc gatcttcatc aca                                              23

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence : Synthetic
      nucleotide (FGF15-F)

<400> SEQUENCE: 11
ccagtggtct tggtgtgctg a                                                21

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence : Synthetic
      nucleotide (FGF15-R)

<400> SEQUENCE: 12
ggcctggatg aagatgatat gga                                              23
```

BILE ACID SYNTHESIS PROMOTER, COMPOSITION FOR PROMOTING BILE ACID SYNTHESIS AND FOOD COMPOSITION FOR PROMOTING BILE ACID SYNTHESIS

CROSS REFERENCE TO RELATED APPLICATION

This is a divisional application of U.S. application Ser. No. 16/493,906, which is a U.S National stage of International Patent Application No. PCT/JP2018/005630, filed on Feb. 19, 2018 which claims priority to Japanese Patent Application No. 2017-050744, filed Mar. 6, 2017. The disclosure of each of these applications is incorporated herein by reference in its entirety.

TECHNICAL FIELD

The present invention relates to a bile acid synthesis promoter, a composition for promoting bile acid synthesis and a food composition for promoting bile acid synthesis which can promote the synthesis of bile acid from cholesterol in the liver.

BACKGROUND ART

Cholesterol is an important component concerning various physiological phenomena of the living body. However, an excess amount of cholesterol in the blood is known to cause lifestyle-related diseases such as arteriosclerosis. Cholesterol forms a complex with proteins in the blood and exists as lipoprotein. Among this lipoprotein, low-density lipoprotein cholesterol (LDL cholesterol) is said to promote arteriosclerosis. Therefore, it is considered that arteriosclerosis can be ameliorated by reducing lipid in the blood, particularly LDL cholesterol.

Cholesterol s converted into bile acid in the liver and excreted from the bowel. The bile acid synthesis is a main mechanism to eliminate extra cholesterol outside the body. It is considered that various symptoms caused by increased blood cholesterol can be treated, ameliorated or prevented by promoting such conversion of cholesterol into bile acid.

Cholesterol is converted into bile acid in the liver by bile acid synthetic enzymes such as CYP7A1 and CYP8B1 (non-patent document 1). Bile acid is excreted partly after being secreted into the intestinal tract. The remaining bile acid is reabsorbed from the bowel and returns to the liver. Bile acid is recycled by circulating between the liver and the intestinal tract. The conversion of cholesterol into bile acid is regulated by bile acid which is reabsorbed and returned to the liver. Bile acid returned to the liver binds to FXR (farnesoid X receptor) which is a nuclear receptor and activate it. Activated FXR induces the expression of SHP (small heterodimer partner) which is another nuclear receptor. SHP has the action to inhibit the expression of bile acid synthetic enzyme genes such as Cyp7a1 and Cyp8b1. In addition, FXR promotes the expression of FGF15 (Fibroblast growth factor 15) in the intestinal tract. FGF15 inhibits the expression of Cyp7a1 and Cyp8b1 which are bile acid synthetic enzyme genes by binding to receptor FGF4 of the liver to activate it.

As a medicine to promote lipid metabolism, an agent for improving lipid metabolism which include krill protein as an active ingredient is disclosed, for example, in patent document 1. The agent for improving lipid metabolism described in patent document 1 reduces blood cholesterol by cholesterol absorption inhibition or bile acid excretion effect.

CITATION LIST

Patent Literature

Patent Literature 1: JP-A-2010-095456

Non-Patent Literature

Non-Patent Literature 1: Hepatology, 2012, Vol. 56, No. 3, p. 1034-1043.

SUMMARY OF INVENTION

Technical Problem

The present invention is intended to provide a novel medicine that is capable of promoting cholesterol metabolism to thereby treat, ameliorate or prevent various symptoms associated with increase in blood cholesterol level.

Solution to Problem

The present inventors found that the amount of bile acid was increased in comparison with control group when measuring the amount of bile acid in feces of the leptin receptor-deficient model administered arctigenin. They also found that Cyp8b1, which is a bile acid synthetic enzyme, is positively regulated and SHP, FXR and FGF4R of the liver, which have the action to inhibit the bile acid synthesis, as well as small intestinal FGF15 and SHP are negatively regulated in arctigenin administrated group (AG group) in comparison with control group. That is, they newly found that arctigenin has an effect to promote conversion of cholesterol into bile acid, and they completed the present invention.

The present invention provides a bile acid synthesis promoter comprising arctigenin and/or arctiin as an active ingredient(s).

The present invention also provides a composition for promoting bile acid synthesis comprising arctigenin and/or arctiin as an active ingredient(s).

The present invention also provides a composition for promoting bile acid synthesis comprising arctigenin and/or arctiin as burdock, burdock fruit, burdock sprout or Forsythia fruit or extracts thereof in the above composition for promoting bile acid synthesis.

The present invention also provides a food composition for promoting bile acid synthesis comprising arctigenin and/or arctiin as an active ingredient(s).

The present invention also provides a food composition for promoting bile acid synthesis comprising arctigenin and/or arctiin as burdock, burdock fruit, burdock sprout or Forsythia fruit or extracts thereof in the above food composition for promoting bile acid synthesis.

The present invention also provides an expression promoter of bile acid synthetic enzymes comprising arctigenin and/or arctiin as an active ingredient(s).

The present invention also provides a bile acid excretion promoter comprising arctigenin and/or arctiin as an active ingredient(s).

The present invention also provides a cholesterol metabolism promoter in the liver comprising arctigenin and/or arctiin as an active ingredient(s).

Advantageous Effects of Invention

Since the present invention has an action to promote the bile acid synthesis, it can promote cholesterol metabolism to thereby treat, ameliorate or prevent various symptoms associated with increase in blood cholesterol level.

DESCRIPTION OF EMBODIMENTS

The present invention provides a bile acid synthesis promoter and a composition for promoting bile acid synthesis comprising arctigenin and/or arctiin as an active ingredient(s).

Bile acid is a generic term of steroid derivatives having a cholanic acid backbone synthesized from cholesterol in the liver. In the present invention, bile acid comprises, for example, unbound bile acid such as cholic acid, chenodeoxycholic acid, deoxycholic acid and lithocholic acid; binding bile acid such as taurocholic acid, glycocholic acid, glycochenodeoxycholic acid, taurochenodeoxycholic acid, glycodeoxycholic acid, taurodeoxycholic acid, glycolithocholic acid and taurolithocholic acid, and salts and conjugates thereof. In addition, bile acid in the present invention includes various kinds of bile acid found in bile of mammals, birds, reptiles, amphibians, fishes and the like as well as bile acid found in humans.

The "synthesis of bile acid" as used herein refers to synthesis, conversion or metabolism of cholesterol into bile acid in the liver. "To promote the bile acid synthesis" as used herein includes initiating, quickening, accelerating and increasing the synthesis of bile acid. Promoting the bile acid synthesis can be determined by increase of the amount of bile acid in the liver, decrease of cholesterol in the liver, increase of the amount of bile acid in feces, increase of the expression of bile acid synthetic enzymes and the like.

The bile acid synthesis promoter and the composition for promoting bile acid synthesis of the present invention comprise arctigenin and/or arctiin as an active ingredient(s). Arctigenin and arctiin are one of diphenylpropanoid (lignans) included in plants such as burdock. It is known that arctiin is a precursor of arctigenin and is metabolized in vivo to become arctigenin. As arctigenin and/or arctiin, chemically synthesized arctigenin and/or arctiin may be used, and arctigenin and/or arctiin isolated from plants may be used. In addition, as arctigenin and/or arctiin, a plant itself including arctigenin and/or arctiin or an extract of this plant may be used. Plants including arctigenin and/or arctiin comprise, for example, *Arctium lappa* (burdock) (sprout, leaf, rhizome, burdock fruit), *Forsythia* x *intermedia* (flower, leaf, fruit, rhizome), *Forsythia viridissima* var. *koreana* (flower, leaf, fruit, rhizome), *Forsythia suspense* (Forsythia fruit) (flower, leaf, fruit, rhizome), *Forsythia viridissima* (flower, leaf, fruit, rhizome), *Carthamus tinctorius, Centaurea cyanus, Cirsium vulgare, Centaurea benedicta (Cnicus benedictus), Cynara cardunculus, Onopordum acanthium,* thistle (Aniurokoazami), *Sesamum indicum, Ipomoea cairica, Polygala chinensis, Trachelospermum asiaticum* var. *glabrum, Trachelospermum asiaticum, Trachelospermum gracilipes* var. *liukiuense, Trachelospermum gracilipes, Trachelospermum jasminoides, Trachelospermum jasminoides* var. *pubescens, Wikstroemia indica, Persicaria orientalis, Cerasus jamasakura, Arabidopsis thaliana,* amaranth, *Juglans* (walnut), *Arena sativa* (oat), *Triticum spelta,* soft wheat, *Cupressus lusitanica* and *Torreya nucifera.* Above all, burdock (particularly burdock fruit and burdock sprout) and Forsythia fruit (particularly leaf) are preferable because they have high content of arctigenin and/or arctiin. When using a plant itself, the plant which is raw or dried and chopped or is dried and powdered can be used.

When using an extract of a plant as arctigenin and/or arctiin, the extract may be prepared from the plant, for example, by following method. The extract as used in the present invention may be extracted, for example, from a plant including arctigenin and/or arctiin by two steps of an enzymatic conversion step and an extraction step using an organic solvent.

The enzymatic conversion step is a step enzymically converting arctiin included in the plant into arctigenin by β-glucosidase, which is an endogenous enzyme in the plant. Specifically, the plant which was dried and cut is kept at an appropriate temperature to make endogenous β-glucosidase act and advance the reaction from arctiin to arctigenin. For example, the plant can be kept at a certain temperature by adding any solution such as water to the cut plant and stirring them at a temperature of around 30° C. (20 to 50) and the like.

The extraction step using an organic solvent is a step to extract arctigenin and arctiin from a plant using any appropriate organic solvent. That is, it is a step to extract an extract (extract) from a plant by adding an appropriate solvent in the condition that arctigenin became the high content through the enzymatic conversion step described above. For example, an appropriate solvent is added to the plant and then heated and stirred for an appropriate period of time, and an extract is extracted. Furthermore, the extract can be extracted using any extraction method well known to those skilled in the art, such as heating to reflux, drip extraction, immersion extraction or the pressurized extraction, instead of heating and stirring.

Because arctigenin is water-insoluble, the yield of arctigenin can be improved by adding an organic solvent. As the organic solvent, any organic solvent can be used. For example, alcohol such as methanol, ethanol and propanol, and acetone can be used. Considering from a safety standpoint, it is preferable to use 30% ethanol as the organic solvent. When the solvent is evaporated from the extract, a paste-like concentrate is obtained and a dried product can be obtained by further drying the concentrate.

The bile acid synthesis promoter and the composition for promoting bile acid synthesis of the present invention can be pharmaceutical preparations in any form. The bile acid synthesis promoter and the composition for promoting bile acid synthesis can be, as oral administration pharmaceutical preparations, for example, tablet such as dragee, buccal tablet, coat tablet and chewable tablet; troche; pill; powdered drug; capsule including hard capsule and soft capsule; granule; and liquid such as suspension, emulsion, syrup, elixir and the like.

In addition, the bile acid synthesis promoter and the composition for promoting bile acid synthesis of the present invention can be pharmaceutical preparations for parenteral administration such as intravenous injection, subcutaneous injection, intraperitoneal injection, intramuscular injection, transdermal administration, nasal administration, transpulmonary administration, enteral administration, buccal administration and transmucosal administration. For example, the bile acid synthesis promoter and the composition for promoting bile acid synthesis of the present invention can be injection, transdermal absorption tape, aerosol, suppository and the like.

The bile acid synthesis promoter and the composition for promoting bile acid synthesis of the present invention can also be provided as the external preparation. The external preparation of the present invention can be pharmaceuticals, cosmetics and the like. The external preparation of the present invention can be an external preparation to apply to skin, scalp, hair, mucous membrane, nail and the like. The external preparation includes, for example, liniments such as creams, ointments, liquids, gels, lotions, emulsions, aerosols, sticks, seat masks, solids, foams, oils and hard gel sticks; patches such as cataplasms, plasters, tapes and patches; sprays and the like.

The bile acid synthesis promoter and the composition for promoting bile acid synthesis of the present invention can also be in a form suitable for foods and may be, for example, solid form, liquid form, granular form, grainy form, powder form, capsule form, creamy form, paste form and the like.

The composition for promoting bile acid synthesis of the present invention can be a composition used for pharmaceuticals, cosmetics, foods and the like. The composition for promoting bile acid synthesis of the present invention can further include any components commonly used for pharmaceuticals, cosmetics and foods. For example, the composition for promoting bile acid synthesis of the present invention may further include a base, a carrier, a excipient, a binder, a disintegrating agent, a lubricant, a coloring agent and the like which are pharmaceutically acceptable.

Examples of the carrier and the excipient used for the composition for promoting bile acid synthesis include lactose, glucose, white soft sugar, mannitol, dextrin, potato starch, corn starch, calcium carbonate, calcium phosphate, calcium sulfate, crystalline cellulose and the like.

Examples of the binder include starch, gelatin, syrup, tragacanth gum, polyvinyl alcohol, polyvinyl ether, polyvinylpyrrolidone, hydroxypropylcellulose, methylcellulose, ethylcellulose, carboxymethylcellulose and the like.

Examples of the disintegrating agent include starch, agar, gelatin powder, crystalline cellulose, calcium carbonate, sodium hydrogen carbonate, sodium alginate, sodium carboxymethylcellulose, calcium carboxymethylcellulose and the like.

Examples of the lubricant include magnesium stearate, hydrogenated vegetable oil, talc, macrogol and the like. As the coloring agent, any coloring agent which has been accepted to be added to pharmaceuticals, cosmetics and foods can be used.

In addition, the composition for promoting bile acid synthesis, if required, may be coated with one or more layers of white soft sugar, gelatin, refined shellac, gelatin, glycerin, sorbitol, ethylcellulose, hydroxypropylcellulose, hydroxypropylmethylcellulose, polyvinylpyrrolidone, cellulose acetate phthalate, hydroxypropylmethylcellulose phthalate, methyl methacrylate, methacrylic acid polymer and the like.

Moreover, if required, a pH-controller, a buffering agent, a stabilizer, a preservative, an antiseptic, a diluent, a coating agent, a sweetener, an aroma, a solubilizing agent and the like may be added to the composition for promoting bile acid synthesis.

The present invention also provides pharmaceuticals comprising the composition for promoting bile acid synthesis of the present invention. Pharmaceuticals of the present invention can be pharmaceuticals to promote the synthesis of cholesterol into bile acid. Pharmaceuticals of the present invention can also be pharmaceuticals to treat, ameliorate and prevent various kinds of symptoms associated with increase in blood cholesterol level, and for example, it can be pharmaceuticals to treat, ameliorate and prevent dyslipidemia, arteriosclerosis, angina, myocardial infarction, stroke, cerebral infarction and cerebral hemorrhage.

The present invention also provides a food composition for promoting bile acid synthesis comprising arctigenin and/or arctiin as an active ingredient(s). The food composition for promoting bile acid synthesis of the present invention can be composed in a manner similar to those of the bile acid synthesis promoter and the composition for promoting bile acid synthesis described above. The food composition of the present invention can be a food composition for ameliorating or preventing diseases such as dyslipidemia, arteriosclerosis, angina, myocardial infarction, stroke, cerebral infarction and cerebral hemorrhage and conditions thereof.

The "food composition" as used herein includes foods for the ill, health foods, functional foods, foods for specified health use, dietary supplements, supplements and the like as well as general foods and drinks. Examples of the general foods and drinks include various drinks, various foods, processed foods, liquid foods (soups and the like), seasonings, nutrition-supplement drinks, snacks and the like. The "processed foods" as used herein mean foods obtained by processing and/or cooking natural foodstuffs (animals and plants, and the like) and include, for example, processed meat, processed vegetables, processed fruits, frozen foods, retort-pouched foods, canned foods, bottled foods, instant foods and the like. The food composition of the present invention may be a food with an indication saying that the bile acid synthesis is promoted or the cholesterol metabolism is promoted. The food composition of the present invention may also be provided in a form contained in a bag, a container and the like. The bag and the container used in the present invention can be any bag and any container which are generally used for foods.

The content of arctigenin and/or arctiin in the bile acid synthesis promoter, the composition for promoting bile acid synthesis and the food composition for promoting bile acid synthesis of the present invention should be the amount that an effect to promote the bile acid synthesis can be exerted and can be set depending on subjects to apply, purposes and administration methods (intake methods) appropriately. For example, when making humans ingest, preferably, arctigenin and/or arctiin can be included so that an intake per day becomes 10 to 2000 mg.

The present invention also provides the expression promoter of bile acid synthetic enzymes which contains arctigenin and/or arctiin as an active ingredient(s). The bile acid synthetic enzymes include, for example, CYP7A1, CYP8B1 and the like. Arctigenin has the action to promote the expression of bile acid synthetic enzymes as shown in examples described below. Arctigenin also has the action to inhibit the expression of various kinds of factors such as SHP, FXR, FGF4R and FGF15 with action to negatively regulate the expression of bile acid synthetic enzymes.

"To promote the expression" of gene as used herein means, for example, to increase the amount of transcription products derived from genes, to increase the amount of proteins derived from genes and the like. In addition, "to inhibit the expression" as used herein means, for example, to decrease the amount of transcription products derived from genes and to decrease the amount of proteins derived from genes.

The expression promoter of bile acid synthetic enzymes of the present invention may contain arctigenin and/or arctiin as burdock, burdock fruit, burdock sprout or Forsythia fruit or extracts thereof. The expression promoter of bile acid synthetic enzymes of the present invention can also be composed in manners similar to those of the bile acid synthesis promoter, the composition for promoting bile acid synthesis and the food composition for promoting bile acid synthesis of the present invention described above.

The expression promoter of bile acid synthetic enzymes of the present invention can promote the synthesis of cholesterol into bile acid by promoting the expression of bile acid synthetic enzymes. Therefore, the expression promoter of bile acid synthetic enzymes of the present invention can improve the cholesterol metabolism to thereby treat, ameliorate or prevent various symptoms associated with increase in blood cholesterol level.

The present invention also provides the bile acid excretion promoter which contains arctigenin and/or arctiin as an active ingredient(s). The "bile acid excretion" as used herein refers to excretion to the outside the body of bile acid and refers to, for example, excreting bile acid in feces from intestinal tract.

The bile acid excretion promoter of the present invention may contain arctigenin and/or arctiin as burdock, burdock fruit, burdock sprout or Forsythia fruit or extracts thereof. The bile acid excretion promoter of the present invention can also be composed in manners similar to those of the bile acid synthesis promoter, the composition for promoting bile acid synthesis and the food composition for promoting bile acid synthesis of the present invention. The bile acid excretion promoter of the present invention can improve cholesterol metabolism to thereby treat, ameliorate or prevent various symptoms associated with increase in blood cholesterol level.

The present invention also provides the cholesterol metabolism promoter in the liver which contains arctigenin and/or arctiin as an active ingredient(s). The "cholesterol metabolism" as used herein refers to converting cholesterol into another compound, for example, converting cholesterol into bile acid.

The cholesterol metabolism promoter in the liver of the present invention may contain arctigenin and/or arctiin as burdock, burdock fruit, burdock sprout or Forsythia fruit or extracts thereof. The cholesterol metabolism promoter in the liver of the present invention can also be composed in manners similar to those of the bile acid synthesis promoter, the composition for promoting bile acid synthesis and the food composition for promoting bile acid synthesis of the present invention. The cholesterol metabolism promoter in the liver of the present invention can improve cholesterol metabolism to thereby treat, ameliorate or prevent various symptoms associated with increase in blood cholesterol level.

EXAMPLES

Examples are shown below and the embodiments of the present invention are explained further in detail, however the present invention is not limited to the following examples.

(Measurement of Enzymatic Activity)

The β-glucosidase activities of burdock fruit were measured by the following method. Burdock fruit samples of different origins and different lots were pulverized with a Wiley mill, and the pulverized burdock fruit samples each in an amount of 0.1 g were diluted with 10 mL of water. Sample solutions were thus obtained.

As the substrate solution, 20 mmol/L p-nitrophenyl-β-D-glucopyranoside aqueous solution was prepared by adding water to 0.15 g of p-nitrophenyl-β-D-glucopyranoside and obtain the constant volume of 25 mL. 0.5 mL of 20 mmol/L p-nitrophenyl-β-D-glucopyranoside aqueous solution was added to 1 mL of 0.1 mol/L acetic acid buffer, and a reaction mixture was thus prepared, and then preheated at 37° C. for approximately five minutes.

After adding 0.5 mL of sample solution to the reaction mixture and advancing the reaction at 37° C. for 15 minutes, the reaction was stopped by adding 2 mL of 0.2 mol/L sodium carbonate aqueous solution, which is a solution to stop the reaction. The absorbance of this liquid at 400 nm was measured, and the enzymatic activity was determined using the following equation from the variation from the value of the blank solution which was not subjected to the enzymatic reaction.

Enzymatic activity (U/g)=(absorbance of sample solution−absorbance of blank solution)×4 mL×1/18.1 (millimolar molecular extinction coefficient of p-nitrophenol under the above measurement conditions: $cm^2/\mu mol$)×1/optical path length (cm)×1/reaction period (minute)×1/0.5 mL×1/concentration of sample solution (g/mL).

Example 1

Production of Burdock Fruit Extract 1

As an example of the composition for promoting bile acid synthesis of the present invention, an extract (extract) was extracted from burdock fruit. After cutting burdock fruit (enzymatic activity of 8.23 U/g), the pieces which completely passed through a sieve of 9.5 mm were further passed through a sieve of 0.85 mm, and it was confirmed that 75% thereof remained. To 560 L of water which was kept at 29 to 33° C., 80 kg of the cut burdock fruit pieces were added, and the mixture was stirred for 30 minutes. Then, 265 L of ethanol was added, and the solution was heated to 85° C. and refluxed by heating for 60 minutes. This solution was centrifuged, and a liquid burdock fruit extract was obtained. This operation was repeated twice, and the obtained liquid extracts were combined and concentrated under reduced pressure. Dextrin was added at 25% to the solid contents of the extract, and the mixture was spray dried. The arctigenin and arctiin content were 6.2% and 7.1%, respectively, and burdock fruit extract powder (comprising 20% dextrin) with arctigenin/arctiin (weight ratio)=0.89 was thus obtained.

Example 2

Production of Burdock Fruit Extract 2

As an example of the composition for promoting bile acid synthesis of the present invention, an extract (extract) was extracted from burdock fruit. After cutting burdock fruit (enzymatic activity of 8.23 U/g), and the pieces which completely passed through a sieve of 9.5 mm were further passed through a sieve of 0.85 mm, and it was confirmed that 75% thereof remained. To 560 L of water which was kept at 30 to 33° C., 80 kg of the cut burdock fruit pieces were added, and the mixture was stirred for 30 minutes. Then, 265 L of ethanol was added, and the solution was heated to 85° C. and refluxed by heating for 30 minutes. The solution was centrifuged, and a liquid burdock fruit extract was obtained. This operation was repeated twice, and the obtained liquid extracts were combined and concentrated under reduced pressure. Dextrin was added at 25% to the solid contents of the extract, and the mixture was spray dried. The arctigenin and arctiin content were 6.0% and 6.8%, respectively, and burdock fruit extract powder (comprising 20% dextrin) with arctigenin/arctiin (weight ratio)=0.87 was thus obtained.

Example 3

Production of Burdock Fruit Extract 3

As an example of the composition for promoting bile acid synthesis of the present invention, extract (extract) was extracted from burdock fruit. After cutting burdock fruit (enzymatic activity 7.82 U/g), the pieces which completely passed through a sieve of 9.5 mm were further passed through a sieve of 0.85 mm, and it was confirmed that 75% thereof remained. To 560 L of water which was kept at 30 to 32° C., 80 kg of the cut burdock fruit pieces were added, and the mixture was stirred for 40 minutes. Then, 258 L of ethanol was added after 60 minutes, and the solution was heated to 85° C. and refluxed by heating for 30 minutes. The liquid was centrifuged, and a liquid burdock fruit extract was obtained. This operation was repeated twice, and the obtained liquid extracts were combined and concentrated under reduced pressure. Dextrin was added at 25% to the solid contents of the extract, and the mixture was spray dried. The arctigenin and arctiin contents were 6.2% and 6.7%, respectively, and burdock fruit extract powder (comprising 20% dextrin) with arctigenin/arctiin (weight ratio) =0.93 was thus obtained.

Example 4

Production of Burdock Fruit Extract 4

As an example of the composition for promoting bile acid synthesis of the present invention, extract (extract) was extracted from burdock fruit. After cutting burdock fruit (enzymatic activity of 7.82 U/g), the pieces which completely passed through a sieve of 9.5 mm were further passed through a sieve of 0.85 mm, and it was confirmed that 75% thereof remained. To 560 L of water which was kept at 30 to 32° C., 80 kg of the cut burdock fruit pieces were added, and the mixture was stirred for 30 minutes. Then, 253 L of ethanol was added, and the solution was heated to 85° C. and refluxed by heating for 40 minutes. The liquid was centrifuged, and the obtained liquid extract was obtained. This operation was repeated twice, and the obtained liquid extracts were combined and concentrated under reduced pressure. Dextrin was added at 25% to the solid contents of the extract, and the mixture was spray dried. The arctigenin and arctiin contents were 6.4% and 7.2%, respectively, and burdock fruit extract powder (comprising 20% dextrin) with arctigenin/arctiin (weight ratio)=0.89 was thus obtained.

Example 5

Production of *Forsythia viridissima* Leaf Extract 1

As an example of the composition for promoting bile acid synthesis of the present invention, extract (extract) was extracted from *Forsythia viridissima* leaves. To 50 g of finely cut forsythia leaves comprising 2.53% arctiin and 0.76% arctigenin, 350 mL of water was added, and the mixture was kept at 37° C. for 30 minutes. Then, 150 mL of ethanol was added, and extraction with heating was conducted for 30 minutes. The solution was subjected to solid-liquid separation using a 100-mesh sieve and then to freeze drying, and 18.62g of a *Forsythia viridissima* leaf extract having an arctigenin content of 5.62% was thus obtained.

Example 6

Production of *Forsythia viridissima* Leaf Extract 2

As an example of the composition for promoting bile acid synthesis of the present invention, extract (extract) was extracted from *Forsythia viridissima* leaves. To 720 g of finely cut forsythia leaves comprising 7.38% arctiin and 0.78% arctigenin, 5 L of water was added, and the mixture was kept at 37° C. for 30 minutes. Then, 2.16 L of ethanol was added, and extraction with heating was conducted for 30 minutes. The solution was subjected to solid-liquid separation using a 100-mesh sieve and then to freeze drying, and 343.07 g of a *Forsythia viridissima* leaf extract having an arctigenin content of 9.55% was thus obtained.

Example 7

Granules Containing Burdock Fruit Extract Powder

As an example of the composition for promoting bile acid synthesis of the present invention, granules were manufactured using a burdock fruit extract. The granules were manufactured according to the "Japanese Pharmacopoeia", General Rules for Preparations, section Granules. That is, the following components (1) to (3) were prepared and processed into granules. The granules were divided into 1.5 g portions and packed in an aluminum laminated film, and granules comprising 0.5 g of burdock fruit extract powder per one pack were obtained.

| | |
|---|---:|
| (1) Burdock fruit extract powder of Example 2 | 33.3% |
| (2) Lactose | 65.2% |
| (3) Hydroxypropylcellulose | 1.5% |
| Total | 100% |

Example 8

Granules Containing Burdock Fruit Extract Powder

As an example of the composition for promoting bile acid synthesis of the present invention, granules were manufactured using a burdock fruit extract. The granules were manufactured according to the "Japanese Pharmacopoeia", General Rules for Preparations, section Granules. That is, the following components (1) to (3) were prepared and processed into granules. The granules were divided into 3.0 g portions and packed in an aluminum laminated film, and granules comprising 2 g of burdock fruit extract powder per one pack were obtained.

| | |
|---|---:|
| (1) Burdock fruit extract powder of Example 2 | 66.7% |
| (2) Lactose | 30.3% |
| (3) Hydroxypropylcellulose | 3.0% |
| Total | 100% |

Example 9

Tablets Containing Burdock Fruit Extract Powder

As an example of the composition for promoting bile acid synthesis of the present invention, tablets were manufactured using a burdock fruit extract. The tablets were manufactured according to the "Japanese Pharmacopoeia", General Rules for Preparations, section Tablets. That is, the following components (1) to (6) were prepared, and the tablets were obtained.

| | |
|---|---:|
| (1) Burdock fruit extract powder of Example 2 | 37.0% |
| (2) Crystalline cellulose | 45.1% |
| (3) Carmellose calcium | 10.0% |

| | |
|---|---|
| (4) Crospovidone | 3.5% |
| (5) Hydrated silicon dioxide | 3.4% |
| (6) Magnesium stearate | 1.0% |
| Total | 100% |

Example 10

Effect of Arctigenin on Bile Acid Synthesis

[Laboratory Animals]

Using 5-week-old male db/db mice (BKS.Cg−+Leprdb/+Leprdb/Jcl, purchased from CLEA Japan, Inc.) that were leptin receptor-deficient model, the experiments were started after one-week preliminary rearing. The animals were reared under the environment of 23.0±5° C. of temperature, 50.0±10% of humidity and 12 hours of light-dark cycle. The animal experiments were approved by animal care and use committee of Keio University and carried out based on animal experiment rules of Keio University.

[Experimental Method]

After preliminary rearing, mice were divided into two groups of (a) control group and (b) arctigenin administrated group (AG group) (each group n=8), and made AG group intake purified diet combined with arctigenin (>98.0%) 0.2% and purified diet (AIN-93G) for control group freely for nine weeks. After administration, 18-hour fasting was performed, and blood specimens were collected from abdominal vena cava under anesthesia, and the liver and the small intestine were sampled.

[Measurement of the Amount of Bile Acid in Feces]

Figure 1:
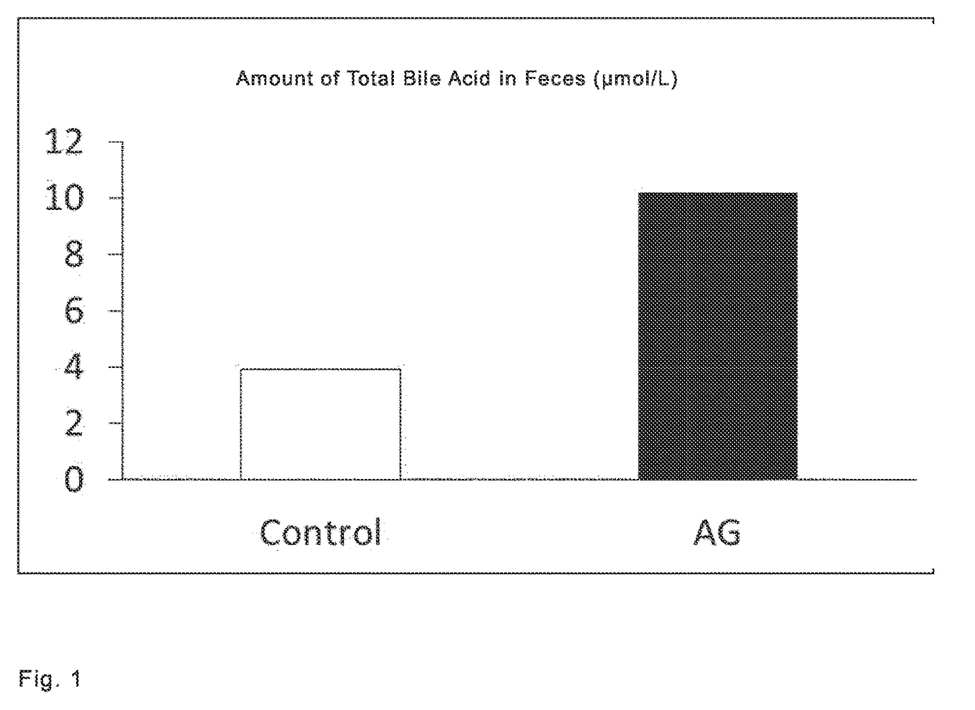
FIG. 1 A graph showing the amount of bile acid in feces in control group and AG group (μmol/L).

Feces were collected from the rearing cage of each group at the end of the administration period, and the amount of bile acid in feces was measured. 10 mg of dry powder of pooled feces was suspended in 0.2 mL of 90% ethanol and incubated at 65° C. for 1 hour, and the supernatant after centrifugation and the washing of the precipitates were collected together. After evaporating the solvent to dryness, 0.5 mL of 90% ethanol was added to the residue and dissolved, and thus a sample for the measurement was obtained. Ultra-performance liquid chromatography tandem mass spectrometry (UPLC-MS/MS, made by Waters) was used for the measurement. FIG. 1 is a graph showing the amount of bile acid in feces (μmol/L) in control group and AG group. In AG group, there was large amount of total bile acid in feces in comparison with control group.

[Measurement of Total Cholesterol in Liver]

Homogenate the liver obtained from each group and extracted total lipid using a lipid extraction kit (Lipid Extraction Kit (Chloroform-Free), Cell Biolabs, Inc.). A total cholesterol level was measured from lipid extract using cholesterol E-test Wako (Wako Pure Chemical Corporation).

Figure 2:
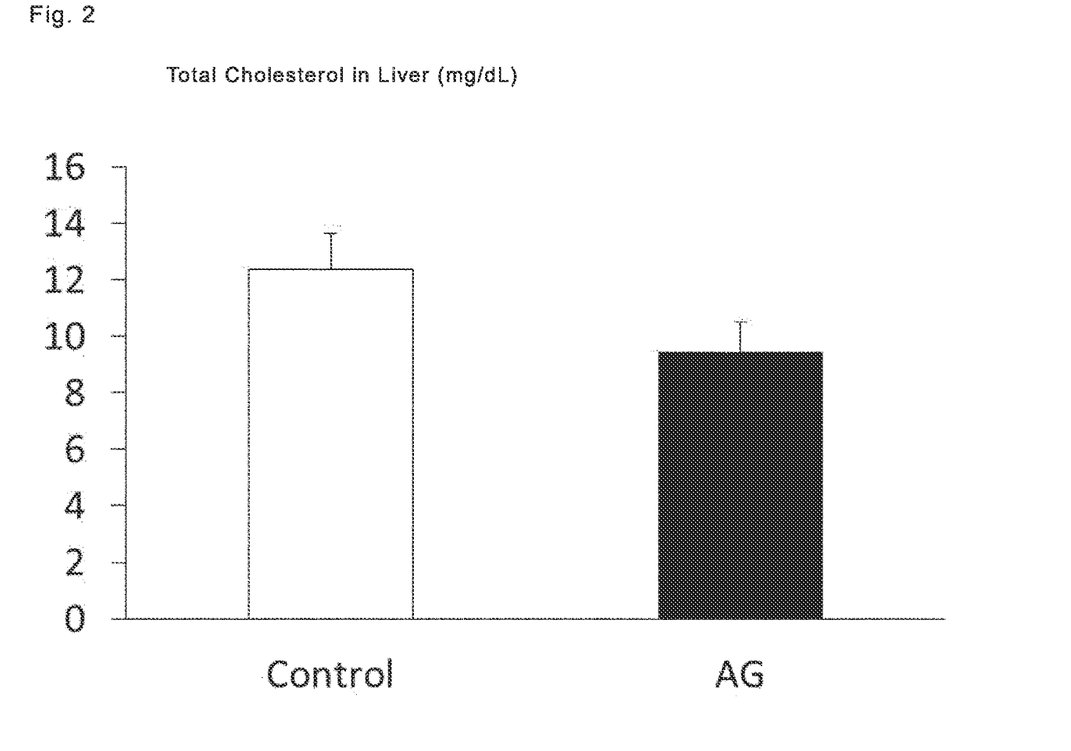
FIG. 2 A graph showing the amount of total cholesterol (mg/dL) in the liver in control group and AG group.

FIG. 2 is a graph showing the amount of total cholesterol in the liver (mg/dL) in control group and AG group. In AG group, there was little amount of total cholesterol in the liver than control group.

[Expression Level of Liver Cholesterol Metabolism-Related Genes]

After having performed extraction of total RNA from the obtained organs and cDNA synthesis on each group, the expression level of Cyp8b1, SHP, FXR and FGF4R of the liver which are the liver cholesterol metabolism-related genes and small intestinal FGF15 and SHP were compared by qPCR. As control, 18S rRNA was used. As the primer for qPCR, 18S (F: TTCTGGCCAACGGTCTAGACAAC (SEQ ID NO: 1), R: CCAGTGGTCTTGGTGTGCTGA (SEQ ID NO: 2)), Cyp8b1 (F: GGAAGCCAAGAAGTCGTTCA (SEQ ID NO: 3), R: GACGCAGACTCTCCTCCATC (SEQ ID NO: 4)), SHP (F: CAAGGAGTATGCGTACCTGAAG (SEQ ID NO: 5), R: GGCTCCAAGACTTCACACAGT (SEQ ID NO: 6)), FXR (F:CAAAATGACTCAGGAG-GAGTACG (SEQ ID NO: 7), R: GCCTCTCTGTCCTT-GATGTATTG (SEQ ID NO; 8)), FGF4R (F:GAGG-CATGCAGTATCTGG (SEQ ID NO: 9), R: CAAAGTCAGCGATCTTCATCACA (SEQ ID NO: 10)), FGF15(F: CCAGTGGTCTTGGTGTGCTGA (SEQ ID NO: 11), R: GGCCTGGATGAAGATGATATGGA (SEQ ID NO: 12)) were used.

Figure 3:
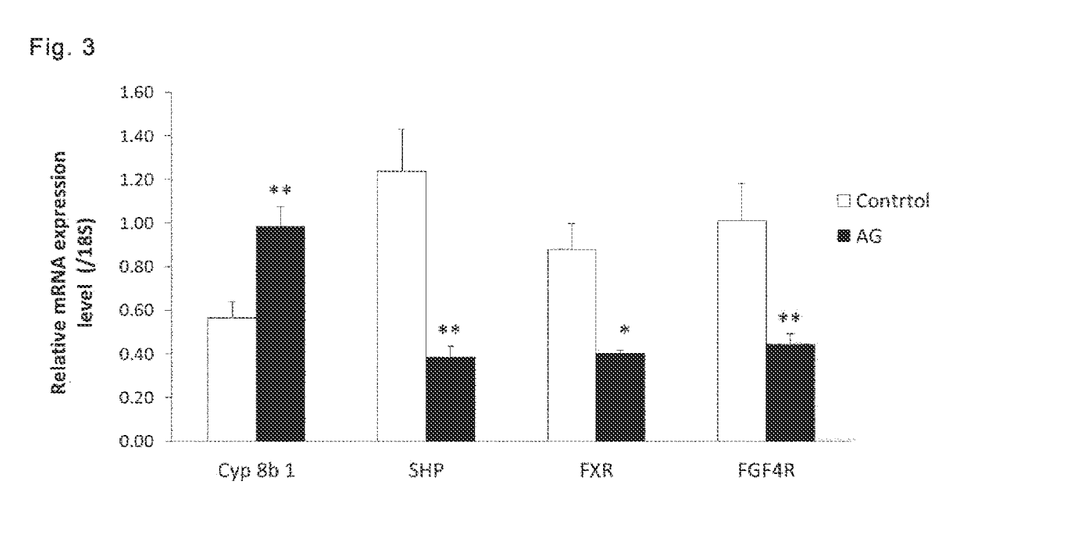
FIG. 3 A graph showing the relative mRNA expression of Cyp8b1, SHP, FXR and FGF4R of the liver in control group and AG group.

FIG. 3 shows relative mRNA expression level of Cyp8b1, SHP, FXR and FGF4R of the liver in control group and AG group. The value in FIG. 3 represents means of six mouse±standard errors (Mean±S.E.M). As a result of Student's t-test, "*" is given when the p value was smaller than 0.05, and "**" was given when the p value was smaller than 0.01. In AG group, in comparison with control group, expression level of Cyp8b1 was significantly high and expression level of SHP, FXR and FGF4R was significantly low.

Figure 4:
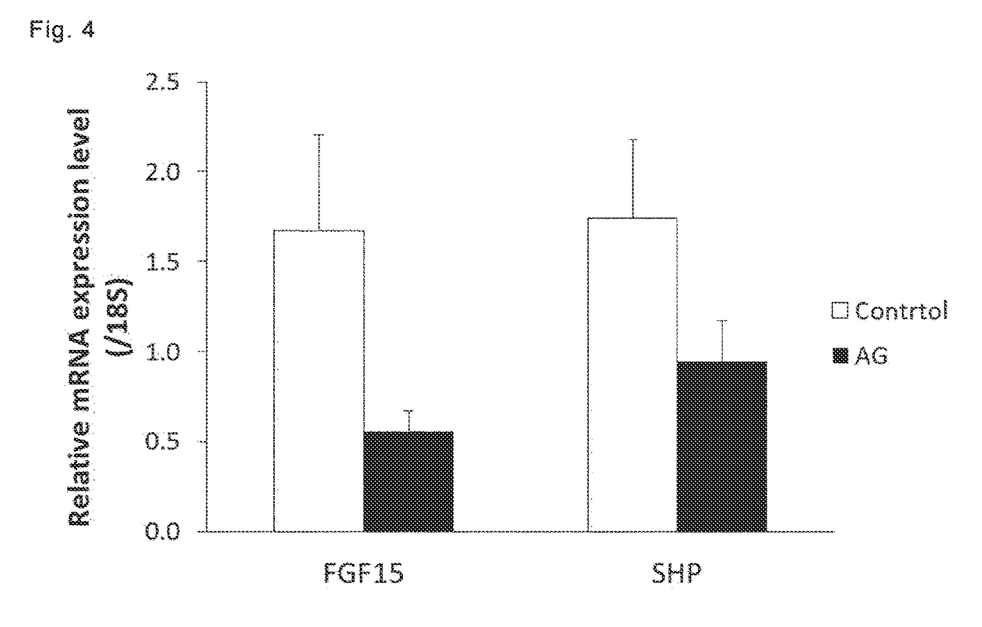
FIG. 4 A graph showing the relative mRNA expression of small intestinal FGF15 and SHP in control group and AG group.

FIG. 4 shows relative mRNA expression level of small intestinal FGF15 and SHP in control group and AG group. In AG group, in comparison with control group, expression level of small intestinal FGF15 and SHP was low.

From these results, it was shown that arctigenin inhibits the expression of SHP, FXR and FGF4R of the liver and small intestinal FGF15 and SHP while promoting the expression of Cyp8b1 of the liver. Therefore, it was strongly suggested that arctigenin promote the cholesterol metabolism in the liver and has the action to promote the synthesis and the excretion of bile acid.

INDUSTRIAL APPLICABILITY

Since the present invention can promote metabolism of cholesterol by promoting bile acid synthesis, it can preferably be used for pharmaceuticals, foods and the like to treat, ameliorate or prevent various kinds of symptoms associated with the cholesterol increase.

Sequence Listing Free Text

The invention claimed is:

1. A method for promoting bile acid excretion comprising:
   administering a pharmaceutically effective amount arctigenin and/or arctiin to a subject in need of such treatment, wherein the subject in need of such treatment is a person diagnosed with angina or cerebral hemorrhage.

2. The method according to claim 1, comprising said arctigenin and/or arctiin as burdock, burdock fruit, burdock sprout or Forsythia fruit or extracts thereof.

3. The method according to claim 1, comprising administering parenterally.

4. The method according to claim 1, comprising administering orally.

* * * * *

UNITED STATES PATENT AND TRADEMARK OFFICE
CERTIFICATE OF CORRECTION

PATENT NO. : 11,554,133 B2
APPLICATION NO. : 17/171545
DATED : January 17, 2023
INVENTOR(S) : Shimpei Watanabe et al.

It is certified that error appears in the above-identified patent and that said Letters Patent is hereby corrected as shown below:

In the Claims

Column 15, Line 63 (Claim 1), please change "amount" to -- amount of --.

Signed and Sealed this
Eleventh Day of July, 2023

Katherine Kelly Vidal
*Director of the United States Patent and Trademark Office*